(12) United States Patent
Wenk et al.

(10) Patent No.: US 7,071,345 B2
(45) Date of Patent: Jul. 4, 2006

(54) METHOD FOR PREPARING CONJUGATED POLYUNSATURATED FATTY ACID ESTERS

(75) Inventors: Hans Henning Wenk, Freising (DE); Katrin Haeser, Puchheim (DE)

(73) Assignee: Bioghurt Biogarde GmbH & Co. KG, Freising (DE)

( * ) Notice: Subject to any disclaimer, the term of this patent is extended or adjusted under 35 U.S.C. 154(b) by 0 days.

(21) Appl. No.: 10/971,710

(22) Filed: Oct. 25, 2004

(65) Prior Publication Data

US 2005/0143591 A1 Jun. 30, 2005

(30) Foreign Application Priority Data

Oct. 23, 2003 (DE) ................................ 103 49 455

(51) Int. Cl.
*C07C 51/353* (2006.01)
(52) U.S. Cl. .................................................. 554/125
(58) Field of Classification Search ................. 554/125
See application file for complete search history.

(56) References Cited

FOREIGN PATENT DOCUMENTS

| DE | 11 56 788 B | 11/1963 |
|---|---|---|
| WO | WO 03/022964 A1 | 3/2003 |

*Primary Examiner*—Deborah D. Carr
(74) *Attorney, Agent, or Firm*—Rothwell, Figg, Ernst & Manbeck pc

(57) ABSTRACT

The claimed method for preparing conjugated polyunsaturated fatty acid esters consisting of an alcohol radical $R_1$ having from 1 to 5 carbon atoms and a fatty acid radical $R_2$ having from 10 to 24 carbon atoms, together with alkoxides having from 1 to 5 carbon atoms, comprises carrying out the reaction solvent-free using a phase-transfer catalyst. In this method, the contents of the fatty acid ester should be from 85 to 99.9% by weight, those of the alkoxide component from 0.05 to 10% by weight, and those of the phase-transfer catalyst from 0.05 to 5.0% by weight, in each case based on the total reaction mixture. Esters of linoleic acid and linolenic acid are preferred as starting material, just as sodium or potassium methoxide or sodium or potassium ethoxide are preferred as alkoxide. Suitable phase-transfer catalysts are, for example, polyethylene glycols, polyethylene glycol monomethyl ethers or polyethylene glycol dimethyl ethers, crown ethers and quaternary ammonium or phosphonium salts. Using this method, which is preferably carried out in a two-phase system at pressures between 1.0 and 2.0 bar and method temperatures of from 60 to 150° C., products can be obtained in which at least 90% of the theoretically isomerizable double bonds are present in conjugated form. The claimed method is used in particular for producing conjugated linoleic acid methyl esters or linoleic acid ethyl esters and is distinguished, in particular, by an extremely simple and economic procedure.

13 Claims, No Drawings

METHOD FOR PREPARING CONJUGATED POLYUNSATURATED FATTY ACID ESTERS

The present invention relates to a method for preparing conjugated polyunsaturated fatty acid esters.

Within the group of naturally occurring polyunsaturated fatty acids, a distinction is made, depending on the position of the double bonds relative to one another, between fatty acids having isolated double bonds and fatty acids having conjugated double bonds. While there is a natural oversupply of the former fatty acids, conjugated fatty acids occur relatively rarely in natural fats.

Since precisely the conjugated fatty acids have gained increasing importance in recent years from the technological aspect, but also in particular from nutritional aspects, there has been no lack of experiments to convert fatty acids having isolated double bonds into fatty acids having conjugated double bonds using suitable isomerization reactions.

Starting from the observation that conjugated unsaturated derivatives are formed in the hydrogenation of fats, attempts were originally made to carry out the isomerization using catalysts as known from applications to harden fats. Although the active catalysts used for this could be used in small amounts the isomerization achieved did not run quantitatively, and in addition unwanted byproducts, such as polymerized or intramolecularly cyclized byproducts occurred.

Although the isomerization of fatty acids containing isolated double bonds using basic substances has long been known, principally for the quantitative determination of polyunsaturated fatty acids, for example of linoleic acid and linolenic acid, this process variant has also been found to be suitable to produce conjugated fatty acids in the context of an isomerization. Customarily, alkali metal hydroxides or alkali metal alkoxides act on the fatty acids or derivatives thereof in at least equimolar amounts in alcoholic solvents at elevated temperatures.

However, in this case also, it was found to be disadvantageous that side reactions occur to a more or less great extent, principally polymerization and cyclization reactions being observed; the theoretically expected yields of conjugated fatty acids thus cannot be achieved in practice.

To overcome these disadvantages, attempts have been made to change the isomerization conditions, and here in particular the concentration of the alkali metal compounds, the temperature and the reaction time, so as to suppress the side reactions. It was found here that, in particular the type of alkali metal compounds and the alcohol selected, contribute decisively to the success of isomerization.

In recent years, in particular three method variants have established themselves, in which conjugated fatty acids, and in particular a conjugated linoleic acid, are prepared by base catalysis.

In the first method, unconjugated fatty acids or esters thereof are reacted with alkali metal hydroxides or other bases, customarily at atmospheric pressure, in a high-boiling alcohol, for example ethylene glycol (U.S. Pat. No. 2,242, 230), in propylene glycol (for example EP-A 0 838 997, U.S. Pat. No. 5,986,116, EP-A 902 082), in glycerol (see WO 2001/18161), in polyether alcohol (for example WO 2001/51597) and in polyols having a free OH group (U.S. Pat. No. 2,343,644). It is also possible to carry out the reaction in water (for example WO 2001/40419, U.S. Pat. No. 4,164, 501, U.S. Pat. No. 2,350,583 and GB 561 803) under then simultaneously high pressure, the reaction temperatures in the method variants with water as solvent being above 180° C. In all these cases, a superstoichiometric amount of a base component is added, since the base reacts first with the fatty acid or ester thereof to give the salt of the fatty acid in a saponification reaction. Furthermore, a solvent is absolutely necessary to keep the reaction mixture liquid.

Customarily, low-boiling solvents such as water are used for this, with the overall reaction then, however, having to be carried out under high pressures. Using water as solvent, the reaction in addition only proceeds at a sufficient rate at very high temperatures, a relatively high content of unwanted fatty acid isomers being formed.

The second known method for the isomerization of unsaturated fatty acids makes use of selected fatty acid alkyl esters as starting material and uses the corresponding alkoxides, for example fatty acid methyl esters and alkali metal methoxide as isomerization catalysts. Since, in this method, generally the problem of saponification does not occur, usually small amounts of catalyst of approximately 1 to 2% by weight suffice. A disadvantage in this case, however, is that the alkoxides do not dissolve in the fatty acid esters, for which reason it is necessary to use solvents not only for the ester but also for the alkoxide component.

To carry out this isomerization variant, just a few percent of the respective solvent is sufficient, for which consideration comes, in particular, to alcohols, as are already present in the form of esters and alkoxides in the reaction mixture. However, the reaction must be carried out under elevated pressure, since the reaction temperature for the short-chain alcohols is significantly above their respective boiling temperature. In addition, corresponding technical measures must also be taken.

Corresponding reactions of unconjugated fatty acid alkyl esters with alkali metal alkoxides in the presence of the corresponding alcohols as solvent and at temperatures above 100° C. under pressure conditions are disclosed, for example, by U.S. Pat. No. 6,479,683, DE-AS 1 156 788 and also DE-AS 1 156 789.

As a third method variant for the isomerization of unconjugated fatty acid derivatives, a type of reaction has become established in which the unconjugated fatty acid alkyl esters are reacted with alkali metal alkoxides in polar-aprotic solvents.

Corresponding methods are disclosed in DE-OS 2 250 232, DE-OS 2 155 727 and U.S. Pat. No. 3,984,444.

Although these reactions in polar-aprotic solvents proceed at relatively low temperatures, the substances used are in part of toxicological concern and, in addition, are difficult to separate off from the product, which makes this reaction variant unsuitable with regard to use of the products in foods.

As already explained, conjugated linoleic acids, linolenic acids and derivatives thereof in the form of esters are important representatives of the fatty acid (derivatives) group.

Conjugated linoleic acid (CLA) is a mixture of position- and configuration-dependent isomers of octa-decadienoic acid which occur naturally in milk and meat of ruminants.

The abbreviation "CLA" thus essentially comprises C18:2 fatty acids and, in particular, 9-cis-11-trans- and 10-trans-12-cis-octadecadienoic acid.

In addition to its demonstrated beneficial action in carcinogenesis in breast, intestinal, gastric and skin tissues, in which case it acts in particular to modulate lymphocyte and macrophage activities, CLA is also a biologically active constituent for food supplements, in particular in combination with antioxidants.

Overall, CLA is thus a prominent representative of conjugated fatty acids and derivatives thereof.

An example for the preparation of CLA is shown in the method described in WO 2001/51597. Here, an oil enriched with fatty acids is reacted with catalytic amounts of a base component in a medium which contains a polyether alcohol (for example polyethylene glycol) as solvent. The reaction temperature should be above 90° C. Here also, a stoichiometric amount of the base component is initially necessary, in order to convert the oil or the fatty acids into the soap form.

According to U.S. Pat. No. 2,343,644, the conjugation of a fatty polyene proceeds with an excess of a base component and in the presence of an ether of a polybasic alcohol which contains a free OH group. For this, in particular, polyethylene glycol monomethyl ethers come into consideration.

A disadvantage here is the necessity to work with an excess of base and, in addition, this process is restricted to ethers of polybasic alcohols which have a free OH group.

The object of the present method was therefore to provide a method for preparing conjugated polyunsaturated fatty acid esters, in which the reaction of nonconjugated polyunsaturated fatty acid esters consisting of an alcohol radical $R_1$ having from 1 to 5 carbon atoms and a fatty acid radical $R_2$ having from 10 to 24 carbon atoms with $C_{1-5}$-alkoxides plays a central role. This method is to be as simple as possible to carry out; that is to say it is not to be subject to any temperature or pressure restrictions and the starting materials used and also the reaction medium itself are to be restricted to a few components. This is to avoid side reactions with corresponding unwanted products and the conjugated polyunsaturated fatty acid esters obtained with the novel method are to be accessible in sufficient yields and good purities.

This object was achieved by a corresponding method in which the reaction is carried out solvent-free using a phase-transfer catalyst.

Surprisingly, in the performance of this method, the degree of isomerization of the resultant products was found to be regularly greater than 90%, with the reaction conditions being able to be kept relatively simple compared with the known methods of the prior art, since the further reaction conditions such as temperature and pressure make no special requirements of the experimental procedure and the reaction apparatus. It was not to be expected that using this simple reaction procedure, product qualities are achieved which are above the known qualities of comparable methods.

With respect to the fatty acid ester used, amounts of from 85 to 99.9% by weight used and, with respect to the alkoxide used, those of from 0.05 to 10% by weight, in each case based on the total reaction mixture, are found to be particularly suitable. Amounts of the fatty acid ester between 90.0 and 98.0% by weight, and of the alkoxide between 0.5 and 5.0% by weight, again in each case based on the total reaction mixture, are considered particularly preferred.

Although the claimed method, within said limits, can be carried out using a multiplicity of fatty acid esters, a method variant is preferred in which esters of linoleic acid and linolenic acid are used as starting material.

Of the group consisting of alkoxides having from 1 to 5 carbon atoms, sodium and potassium alkoxides, and in particular sodium and potassium methoxide, but also sodium and potassium ethoxide have proved particularly suitable.

In contrast to the previously known methods which either operate using organic solvents or else in the presence of water, the inventive method is carried out solvent-free, with, as a further feature essential to the invention, the use of a phase-transfer catalyst playing an important role. This phase-transfer catalyst increases the solubility of the alkoxide in the fatty acid esters and as a result makes the isomerization possible. At the same time, in contrast to the low-boiling alcohols as solvent, the work is carried out at high pressure, since the vapor pressure of the phase-transfer catalysts is extremely low.

The amount of phase-transfer catalyst used is only subject to economic considerations, with, at all events, amounts of from 0.05 to 5.0% by weight, and particularly preferably amounts of from 0.5 to 1.5% by weight, in each case based on the total reaction mixture, having been found to be particularly suitable. Preferred representatives of phase-transfer catalysts which come into consideration are polyethylene glycols, polyethylene glycol monomethyl ethers or dimethyl ethers, crown ethers, for example 15-crown-5, 18-crown-6, dibenzo-18-crown-6, dicyclohexano-18-crown-6, quaternary ammonium or phosphonium salts, for example benzyltrimethylammonium chloride, cetyltrimethyl-ammonium bromide, tetrabutylammonium bromide, benzyl-triphenylphosphonium bromide, or tetrabutylphosphonium bromide and mixtures thereof, with non-toxic phase-transfer catalysts, for example polyethylene glycols, in particular being suitable.

With respect to the reaction medium, the present invention preferred a variant in which the conjugation is carried out in a two-phase system.

As already repeatedly indicated, the particular advantage of the present method is to be considered to be that no special conditions need to be met with respect to reaction pressure and reaction temperature. However, primarily for economic reasons, a reaction procedure is preferred which is carried out at pressures between 1.0 and 2.0 bar, and particularly preferably at atmospheric pressure. With respect to the method temperatures to be selected, ranges between 60 and 150° C., particularly preferably between 80 and 120° C., and very particularly preferably between 90 and 100° C., are to be considered suitable.

Obviously, the reaction time more and more increases with decreasing reaction temperature. However, it has additionally surprisingly been found that the proportion of unwanted isomers in the product is extremely low when the reaction temperature is selected as low as possible, that is to say in the range around 60° C. Thus, in cases of need, via the selection of the reaction temperature, the degree of isomerization and the ratio of the different isomers can be preselected and controlled. Even at relatively high temperatures (e.g. 100° C.), in the inventive method, unwanted isomers, that is to say in particular isomers other than 9-cis-11-trans- and 10-trans-12-cis-octadeca-dienoic acid, are not detectable, of course, in principle, the double bonds in the unwanted isomers can also be conjugated to one another.

Not least for this reason, the present invention also claims a method variant using which products are obtained in which at least 90%, and in particular at least 95%, of the theoretically isomerizable double bonds are present in conjugated form. In this context it must be noted that the degree of isomerization for example of linoleic acid, in general can be determined unambiguously, since, for example in the case of complete conversion, 100% of the double bonds are conjugated. In the case of linolenic acid and other fatty acids having at least three double bonds, the definition is more difficult, since in these cases isomers can be formed, which can no longer react further, but in which not all double bonds are conjugated.

The present invention also comprises a separation step for the product which is downstream of the actual method. This additional separation step covers at least washing the product with a dilute acid which is preferably a phosphoric acid, and the final drying, preferably in vacuo and/or at elevated temperatures.

On account of the above described nutritionally important properties of conjugated linoleic acid (CLA), the present invention also covers a method in which conjugated linoleic acid methyl esters or conjugated linoleic acid ethyl esters are obtained.

In summary, the proposed method exhibits as advantages its freedom from solvent and the use of phase-transfer catalysts which, used in very small amounts, avoid working under high pressures, with it also being possible, by selecting the respective temperature range, to control in a substantially targeted manner the proportion of the differing isomers. Owing to its simple means of being carried out and the three-component composition, being based on the fatty acid ester, the alkoxides and the phase-transfer catalyst, the proposed method can be carried out extremely economically, products of high quality being obtained, in particular in the form of CLA esters.

The claimed method for preparing conjugated polyunsaturated fatty acid esters consisting of an alcohol radical $R_1$ having from 1 to 5 carbon atoms and a fatty acid radical $R_2$ having from 10 to 24 carbon atoms, together with alkoxides having from 1 to 5 carbon atoms, comprises carrying out the reaction solvent-free using a phase-transfer catalyst. In this method the contents of the fatty acid ester should be from 85 to 99.9% by weight, those of the alkoxide component from 0.05 to 10% by weight, and those of the phase-transfer catalyst from 0.05 to 5.0% by weight, in each case based on the total reaction mixture. Esters of linoleic acid and linolenic acid are preferred as starting material, just as sodium or potassium methoxide or sodium or potassium ethoxide are preferred as alkoxide. Suitable phase-transfer catalysts are, for example, polyethylene glycols, polyethylene glycol monomethyl ethers or polyethylene glycol dimethyl ethers, crown ethers and quaternary ammonium or phosphonium salts. Using this method, which is preferably carried out in a two-phase system at pressures between 1.0 and 2.0 bar and method temperatures of from 60 to 150° C., products can be obtained in which at least 90% of the theoretically isomerizable double bonds are present in conjugated form. The claimed method is used in particular for producing conjugated linoleic acid methyl esters or linoleic acid ethyl esters and is distinguished, in particular, by an extremely simple and economic procedure.

The examples hereinafter verify the advantages of the claimed method for preparing conjugated polyunsaturated fatty acid esters.

EXAMPLES

Example 1 (Comparative Example)

Isomerization without Phase-Transfer Catalyst 50 g of fatty acid methyl ester (76% linoleic acid in the fatty acid portion) were stirred at 100° C. for three hours with 1 g of potassium methoxide. The reaction was terminated by adding 1.0 ml of an 85% phosphoric acid and the product was washed twice with water. An orange liquid was obtained having a degree of isomerization of 6% (determination by gas chromatography).

Example 2 (Inventive)

Isomerization Using a Phase-Transfer Catalyst 20 g of fatty acid ethyl ester (76% linoleic acid in the fatty acid portion) were stirred for 210 minutes with 0.2 g of polyethylene glycol (phase-transfer catalyst having a mean molar mass of 400) and 0.4 g of potassium ethoxide (alkoxide component) and heated to 100° C. under a nitrogen atmosphere. The reaction was then terminated by adding 1.0 ml of an 85% phosphoric acid and the product was washed twice with water. An orange liquid was obtained having a degree of isomerization of 93% (determination by gas chromatography).

Direct comparison of the degree of isomerization of the products of example 1 and example 2 shows the beneficial effect of the phase-transfer catalyst with otherwise virtually identical reaction procedure.

Example 3 (Inventive)

380 g of fatty acid methyl ester (76% linoleic acid in the fatty acid portion) and prepared by trans-esterifying safflower oil with methanol in the presence of 1% potassium hydroxide were heated to 95° C. with 3.82 g of polyethylene glycol (mean molar mass 400) and 5.74 g of potassium methoxide for 210 minutes with vigorous stirring. The entire reaction was carried out under a nitrogen atmosphere. The reaction mixture was finally washed three times each time with 100 ml of a 2% strength phosphoric acid and the product dried in vacuo at 80° C. 370 g of a weakly yellow liquid having a degree of isomerization >99% were obtained. The content of conjugated linoleic acid in the fatty acid portion was determined as 76% using gas chromatography, of which half in each case was 9-cis-11-trans- and 10-trans-12-cis-octadecadienoic acid.

The invention claimed is:

1. A method for preparing conjugated polyunsaturated fatty acid esters by reacting nonconjugated polyunsaturated fatty acid esters consisting of an alcohol radical $R_1$ having from 1 to 5 carbon atoms and a fatty acid radical $R_2$ having from 10 to 24 carbon atoms with alkoxides having from 1 to 5 carbon atoms, which comprises carrying out the reaction solvent-free using a phase-transfer catalyst.

2. The method as claimed in claim 1, wherein from 85 to 99.9% by weight of the fatty acid ester and from 0.05 to 10% by weight of the alkoxide are used, in each case based on the total reaction mixture.

3. The method as claimed in claim 1, wherein from 90.0 to 98.0% by weight of the fatty acid ester and from 0.5 to 5.0% by weight of the alkoxide are used, in each case based on the total reaction mixture.

4. The method as claimed in claim 1, wherein esters of linoleic acid and linolenic acid are used as starting material.

5. The method as claimed in claim 1, wherein a sodium or potassium methoxide or sodium or potassium ethoxide is used as alkoxide.

6. The method as claimed in claim 1, wherein the phase-transfer catalyst is used in amounts of from 0.05 to 5.0% by weight, and particularly preferably in amounts of from 0.5 to 1.5% by weight, in each case based on the total reaction mixture.

7. The method as claimed in claim 1, wherein, as phase-transfer catalyst, use is made of polyethylene glycols, polyethylene glycol monomethyl ethers or polyethylene glycol dimethyl ethers, crown ethers, for example 15-crown-5, 18-crown-6, dibenzo-18-crown-6, dicyclohexano-18-crown-6, quaternary ammonium or phosphonium salts, for example benzyltrimethylammonium chloride, cetyltrimethylammonium bromide, tetrabutylammonium bromide, benzyltriphenylphosphonium bromide or tetrabutylphosphonium bromide and mixtures thereof.

8. The method as claimed in claim 1, wherein the conjugation is carried out in a two-phase system.

9. The method as claimed in claim 1, wherein the reaction is carried out at pressures between 1.0 and 2.0 bar, and particularly preferably at atmospheric pressure.

10. The method as claimed in claim 1, wherein the reaction is carried out at method temperatures of from 60 to 150° C., particularly preferably at from 80 to 120° C., and very particularly preferably between 90 and 100° C.

11. The method as claimed in claim 1, wherein products are obtained in which at least 90% of the theoretically isomerizable double bonds are present in conjugated form.

12. The method as claimed in claim 1, wherein a separation step for the product is provided downstream, which separation step comprises at least washing the product with a dilute acid, preferably a phosphoric acid, and drying, preferably in vacuo and/or at elevated temperatures.

13. The method as claimed in claim 1, wherein conjugated linoleic acid methyl esters or conjugated linoleic acid ethyl esters are obtained.

\* \* \* \* \*